United States Patent
Matsunaga et al.

(10) Patent No.: US 6,451,069 B2
(45) Date of Patent: Sep. 17, 2002

(54) HAIR DYE COMPOSITION

(75) Inventors: Kenichi Matsunaga; Hajime Miyabe; Yukihiro Ohashi, all of Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/809,196

(22) Filed: Mar. 16, 2001

(30) Foreign Application Priority Data

Mar. 17, 2000 (JP) .................................. 2000-076666

(51) Int. Cl.$^7$ ................................. A01K 7/13

(52) U.S. Cl. .................. 8/405; 8/405; 8/406; 8/407; 8/416; 8/423

(58) Field of Search .............. 8/405, 406, 407, 8/416, 423

(56) References Cited

U.S. PATENT DOCUMENTS

| | | | |
|---|---|---|---|
| 3,706,725 A | * 12/1972 | Minoru et al. | 260/157 |
| 3,822,247 A | * 7/1974 | Minoru et al. | 260/157 |
| 5,520,707 A | 5/1996 | Lim et al. | 8/426 |
| 5,733,343 A | 3/1998 | Moeckli | 8/426 |
| 5,879,412 A | 3/1999 | Rondeau et al. | 8/411 |
| 5,888,252 A | 3/1999 | Moeckli | 8/426 |
| 5,980,587 A | 11/1999 | Samain | 8/426 |

FOREIGN PATENT DOCUMENTS

| | | |
|---|---|---|
| JP | 49-24224 | 3/1974 |
| JP | 49-24228 | 3/1974 |
| JP | 58-2204 | 1/1983 |
| JP | 6-192582 | 7/1994 |
| JP | 6-271435 | 9/1994 |
| JP | 8-501322 | 2/1996 |
| JP | 8-507545 | 3/1996 |
| JP | 9-118832 | 5/1997 |
| JP | 10-502946 | 3/1998 |
| JP | 10-194942 | 7/1998 |

* cited by examiner

Primary Examiner—Yogendra N. Gupta
Assistant Examiner—Eisa Elhilo
(74) Attorney, Agent, or Firm—Oblon, Spivak, McClelland, Maier & Neustadt, P.C.

(57) ABSTRACT

Provided is a hair dye composition containing a direct dye (1). This hair dye composition has markedly high hair dyeing power, has less color fade over time and undergoes a smaller change in the color tone of the dye after storage.

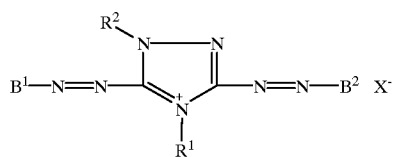

(1)

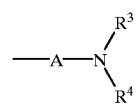

(2)

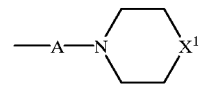

(3)

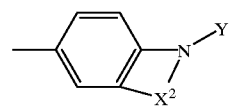

(4)

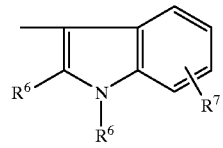

(5)

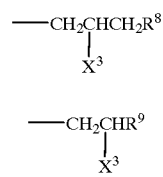

(6)

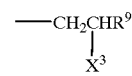

(7)

[$B^1$, $B^2$: the group (2), (3), (4) or (5); $R^1$, $R^2$: the group (6), (7), etc.; $X^-$: anion (A: a (substituted) phenylene group, etc., $R^3$, $R^4$: a (substituted) lower alkyl group, etc.; $X^1$: O, —NH— or $CH_2$-; $X^2$: a (substituted) trimethylene group, etc.; Y: a (substituted) lower alkyl group, etc.; $R^5$: a lower alkyl group, etc.; $R^6$: a lower alkyl group, etc.; $R^7$: H, etc.; $X^3$: —OH, —$NH_2$— or —SH; $R^8$: a lower alkoxy group, etc.; and $R^9$: a phenyl group, etc.)].

9 Claims, No Drawings

HAIR DYE COMPOSITION

TECHNICAL FIELD

The present invention relates to a hair dye composition having markedly high dyeing power, can impart the hair with a vivid and deep color shade ranging from red to blue, has less color fade over time and undergoes a smaller change in the color tone of the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have been found to involve drawbacks that intended dyeing effects are not available owing to decomposition of them caused by mixing, upon hair dyeing, with hydrogen peroxide ordinarily employed as an oxidizing agent; and that they are unstable to an alkali agent or a reducing agent essentially contained in a permanent hair dye.

DISCLOSURE OF THE INVENTION

An object of the present invention is to provide a hair dye composition which has high hair dyeing power, less color fade over time, and excellent storage stability to permit only a smaller change in color tone of the dye after storage.

The present inventors have found that when the below-described cationic dye which is known (Japanese Patent Application Laid-Open (Kokai) No. Sho 49-24224, Sho 49-24228 or Hei 6-192582) to dye therewith polyacrylonitrile fibers, or polyester or polyamide fibers having an acid residue as a dyeing site is used as a hair dye, the resulting dye composition can impart the hair with a vivid and deep color tone ranging from red to blue without decomposing the dye upon hair drying, exhibits excellent light resistance, washing resistance, perspiration resistance, friction resistance and weather resistance, and undergoes a smaller change in the color tone of the dye after storage as compared with that rightly after preparation because the dye exists in the composition stably.

In one aspect of the present invention, there is thus provided a hair dye composition comprising, as a direct dye, a compound represented by the following formula (1):

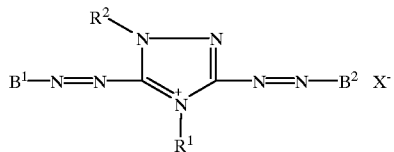

(wherein, $B^1$ and $B^2$ are the same or different and each independently represents a group of the following formula (2), (3), (4) or (5):

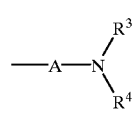

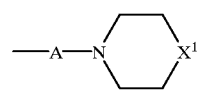

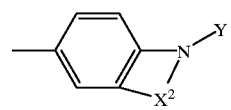

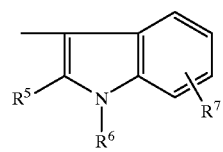

(in which, A represents a phenylene group which may have an unionizable substituent, or a naphthylene group; $R^3$ and $R^4$ are the same or different and each independently represents a hydrogen atom, a $C_{1-4}$ alkyl group which may have a substituent, an aralkyl group or a phenyl group, $X^1$ represents an oxygen atom, an imino group or a methylene group, $X^2$ represents an ethylene or trimethylene group which may have a substituent, Y represents a $C_{1-4}$ alkyl group or aralkyl group which may have a substituent, $R^5$ represents a $C_{1-4}$ alkyl group, or an aryl group, $R^6$ represents a hydrogen atom or a $C_{1-4}$ alkyl group and $R^7$ represents a hydrogen atom or an unionizable group), $R^1$ and $R^2$ are the same or different and each independently represents a $C_{1-4}$ alkyl group, a carbamoylethyl group, a 2-carbamoylpropyl group, a benzyl group or a group of the following formula (6) or (7):

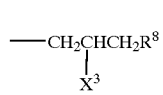

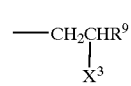

(in which, $X^3$ represents a hydroxyl group, an amino group or a thiol group, $R^8$ represents a hydrogen atom, a halogen atom, a $C_{1-4}$ alkyl group which may have a substituent, a $C_{1-4}$ alkoxy group or a phenoxy group, and $R^9$ represents a hydrogen atom or a phenyl group which may have a substituent), and X⁻ represents an anion.

In another aspect of the present invention, there is also provided a method for dyeing the hair with the above-described hair dye composition.

BEST MODE FOR CARRYING OUT THE INVENTION

Compound (1) is known as a dye for specific synthetic fibers and described in Japanese Patent Application Laid-Open (Kokai) No. Sho 49-24224, Sho 49-24228 or Hei 6-192582. In the present invention, a vivid and deep color shade ranging from red to blue can be imparted to the hair by using this Compound (1) as a direct dye of the hair dye.

In $B^1$ or $B^2$ of the formula (1), examples of A in the formula (2) or (3) include phenylene, chlorophenylene, acetylaminophenylene, methylphenylene, methoxyphenylene and naphthylene. Examples of $R^3$ or $R^4$ in the formula (2) include hydrogen atom, methyl group, ethyl group, cyanoethyl group, hydroxyethyl group, benzyl group, phenyl group, methoxyethyl group and chloroethyl group. Examples of $X^2$ in the formula (4) include trimethylene, 2-hydroxy-trimethylene, 2-chlorotrimethylene, 2-methoxytrimethylene, propylene and 1,1,2-trimethylethylene, while examples of Y in the formula (4) include methyl, butyl, bromoethyl and benzyl. Examples of $R^5$ in the formula (5) include methyl, ethyl, phenyl and tolyl, while those of $R^6$ include hydrogen atom, methyl group and ethyl group. Those of $R^7$ include methyl group, chlorine atom and methoxy group.

Examples of the $C_{1-4}$ alkyl group of $R^1$ or $R^2$ in the formula (1) include methyl and ethyl groups, while those of $R^8$ in the formula (6) include a methyl group, a phenoxy group, a chlorine atom, a methacryloyloxy group, a butoxy group, an ethoxy group and a bromine atom.

Examples of the anion represented by X⁻ in the formula (1) include chloride ions, bromide ions, iodide ions, trichlorozincic acid ions, tetrachlorozincic acid ions, sulfuric acid ions, hydrosulfuric acid ions, methyl sulfate ions, phosphoric acid ions, formic acid ions and acetic acid ions.

Specific examples of the direct dye (1) to be used in the present invention include the following compounds:

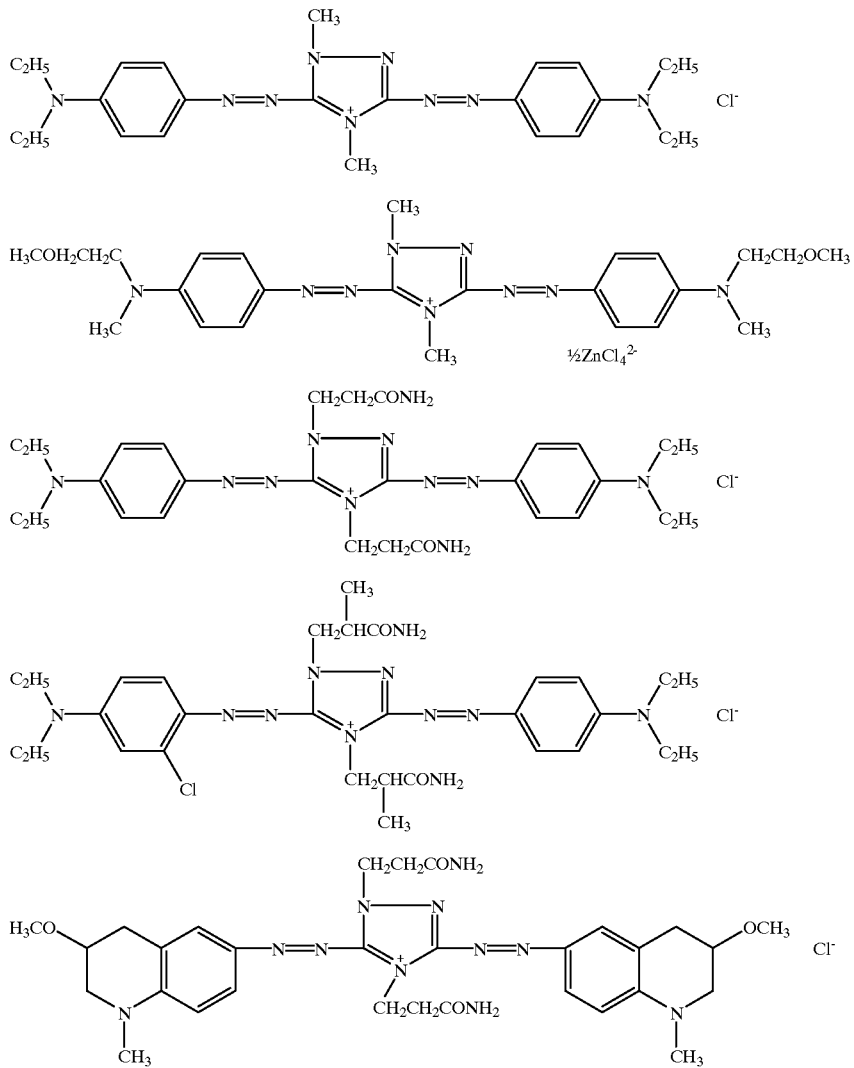

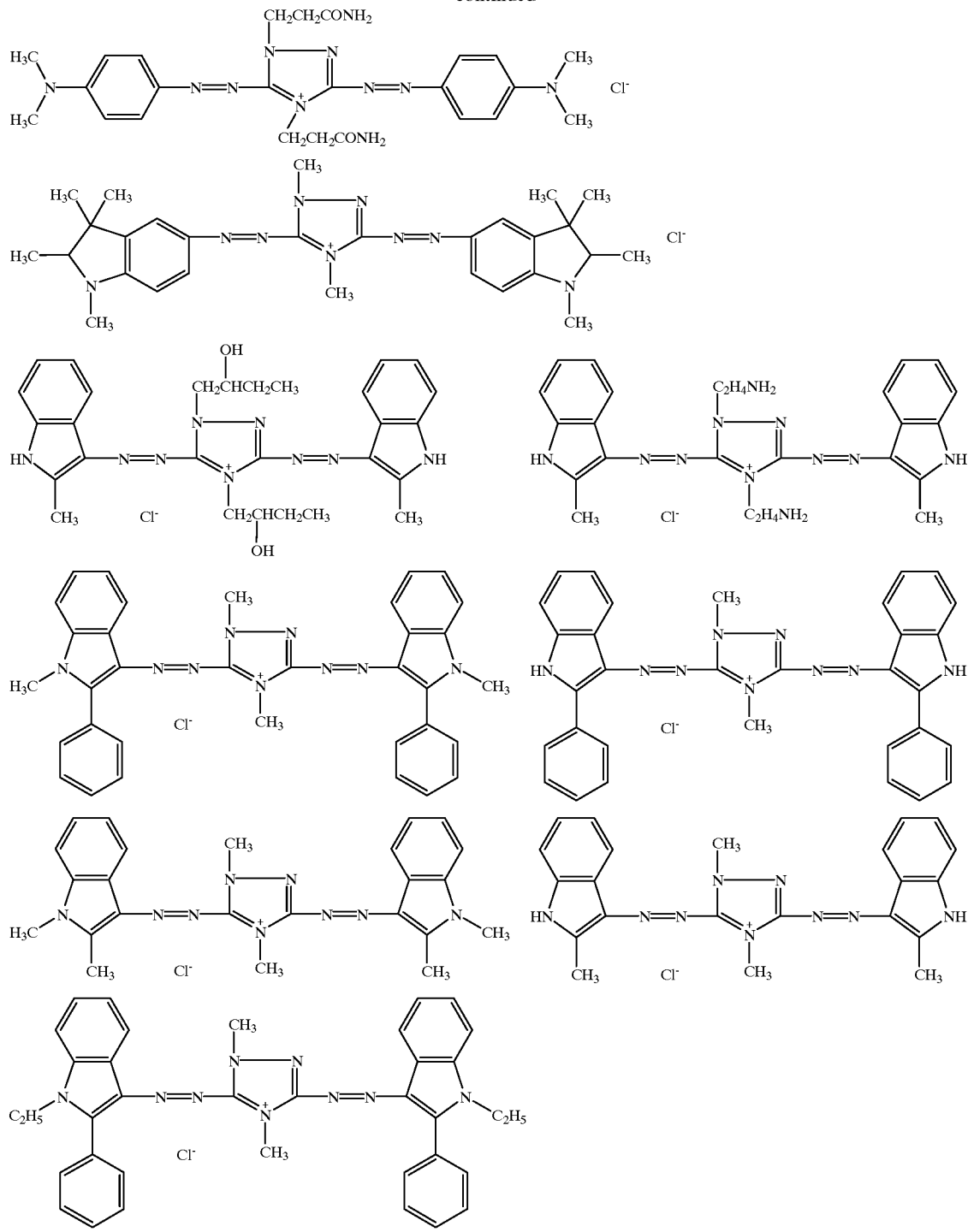
-continued

These direct dyes (1) can be used either singly or in combination with another direct dye. In particular, combination with a yellow dye makes it possible to dye the hair with a deep and highly lustrous dark brown or black color.

Examples of the direct dye other than the direct dyes (1) include Basic Blue 7 (C. I. 42595), Basic Blue 26 (C. I. 44045), Basic Blue 99 (C. I. 56059), Basic Violet 10 (C. I. 45170), Basic Violet 14 (C. I. 42515), Basic Brown 16 (C. I. 12250), Basic Brown 17 (C. I. 12251), Basic Red 2 (C. I. 50240), Basic Red 22 (C. I. 11055), Basic Red 76 (C. I. 12245), Basic Red 118 (C. I. 12251:1) and Basic Yellow 57(C. I. 12719); and basic dyes as described in Japanese Patent Publication No. Sho 58-2204, Japanese Patent Application Laid-Open No. Hei 9-118832, Japanese Language Laid-Open Publication (PCT) No. Hei 8-501322 or Japanese Language Laid-Open Publication (PCT) No. Hei 8-507545.

The direct dye (1) is preferably added in an amount of 0.01 to 20 wt. %, more preferably 0.05 to 10 wt. %, especially 0.1 to 5 wt. % based on the whole composition (after mixture of all the parts when a two part or three part composition is employed; this will apply equally hereinafter). When another direct dye is added in combination, the content of it with the direct dye (1) preferably ranges from 0.05 to 10 wt. %, especially 0.1 to 5 wt. %.

The hair dye composition of the present invention is preferably adjusted to pH 6 to 11, with pH 8 to 11 being especially preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. %, based on the whole composition.

In the hair dye composition of the present invention, an oxidation dye can be incorporated further. This incorporation enables markedly vivid dyeing not attainable by the single use of an oxidation dye. The above-exemplified oxidizing agents can be used as an oxidizing agent, with hydrogen peroxide being particularly preferred. Alternatively, an oxidizing enzyme such as laccase can be employed. For the oxidation dye, known color developers and couplers ordinarily employed for an oxidation type hair dye can be used.

Examples of the developer include p-phenylenediamines having one or several groups selected from $NH_2$—, NHR— and $NR_2$-groups (R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2-methoxyethyl-p-phenylenediamine; 2,5-diaminopyridine derivatives and 4,5-diaminopyrazole derivatives, p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-phenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As a developer or coupler, at least one of the above-exemplified ones can be used. Although no particular limitation is imposed on its content, it is added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of an anionic component/ion activity concentration of a cationic direct dye (1)≦8"

The term "ion activity concentration" as used herein means "molar concentration×ionic valence"

Addition of a polyol, polyol alkyl ether, cationic or amphoteric polymer or silicone to the hair dye composition of the present invention is preferred, because the resulting composition can dye the hair uniformly and has improved cosmetic effects.

In addition to the above-described components, those ordinarily employed as a raw material for cosmetics can be added to the hair dye composition of the present invention within an extent not impairing the advantages of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first-part component containing an alkali agent and a second-part component containing an oxidizing agent, or a third-part composition having, in addition to these two components, a powdery oxidizing agent such as persulfate. The direct dye (1) can be incorporated in either one or both of these components of the two-part or three-part composition. The one-part type is applied to the hair directly, while the two- or three-part type is applied to the hair after mixing these parts upon hair dyeing.

No particular limitation is imposed on the form of the hair dye composition of the present invention. Examples include powder, transparent liquid, emulsion, cream, paste, aerosol, and aerosol foam. It preferably has a viscosity of 2000 to 100000 mPa.s in the stage of application to the hair (after mixing of all the components when a two-part or three-part type is employed).

EXAMPLES

Compounds employed in the below-described examples are as follows:

Compound (a)

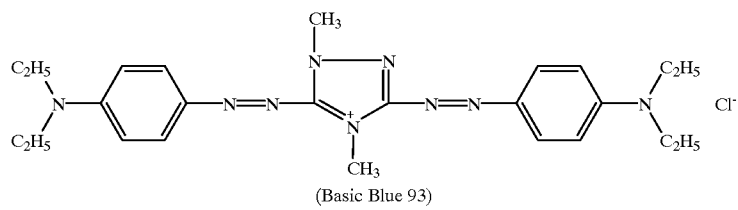

(Basic Blue 93)

Compound (b)

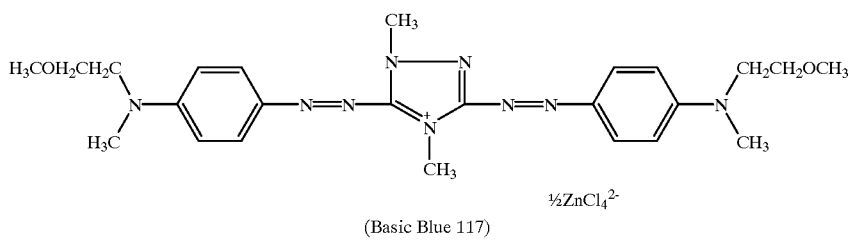

(Basic Blue 117)

Compound (c)

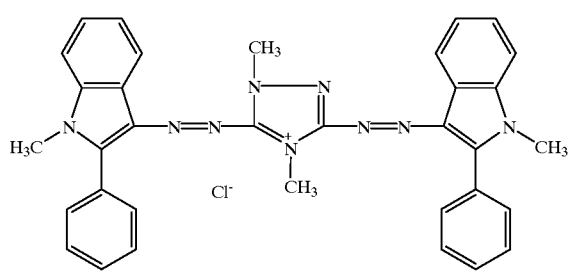

Compound (d)

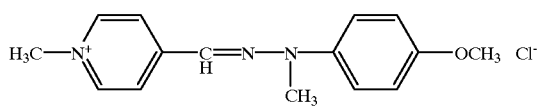

Examples 1 to 5

In a manner known per se in the art, hair dyes as shown in Table 1 were prepared. The data appearing in Table 1 is represented by wt. %.

TABLE 1

| | Examples | | | | |
|---|---|---|---|---|---|
| | 1 | 2 | 3 | 4 | 5 |
| Dye [Compound (a)] | 0.2 | | | 0.1 | |
| Dye [Compound (b)] | | 0.5 | | 0.1 | 0.2 |
| Dye [Compound (c)] | | | 0.3 | | |

TABLE 1-continued

| | Examples | | | | |
|---|---|---|---|---|---|
| | 1 | 2 | 3 | 4 | 5 |
| Dye [Compound (d)] | | | | 0.1 | 0.05 |
| Ethanol | 5 | | | 5 | 5 |
| Propylene glycol | | | 5 | | 5 |
| Diethylene glycol monoethyl ether | 10 | | | | |
| Guar gum | 1 | | | | |
| Hydroxypropyl guar gum | | 1 | 1 | 1 | 1 |
| "Gufquat 734" (trade name, product of ISP Japan) | 1 | | 1 | | |
| "Catinal LC100" (trade name, product of Toho Chemical Industry) | | 1 | | | 1 |
| "Polyether-modified silicone KF6005" (trade name, product of Shin-Etsu Chemical) | | | | | 0.4 |
| "Amodimethicone SM8702C" (trade name, product of Dow Corning Toray Silicone) | | | | 1.5 | |
| Monoethanolamine | | | | 0.1 | |
| Phosphoric acid | Amount to adjust pH to 9 | | | | |
| Perfume | q.s. | | | | |
| Water | balance | | | | |
| Total (g) | 100 | | | | |

Examples 6 to 9

In a manner known per se in the art, hair dyes as shown in Table 2 were prepatred. The data appearing in Table 2 is represented by wt. %.

TABLE 2

|  | Examples | | | |
|---|---|---|---|---|
|  | 6 | 7 | 8 | 9 |
| 1st part | | | | |
| Dye [Compound (a)] | 0.2 | 0.1 | 0.15 | |
| Dye [Compound (b)] | | 0.1 | 0.15 | |
| Dye [Compound (c)] | | | | 0.2 |
| Dye [Compound (d)] | | 0.1 | | |
| 28 wt. % aqueous ammonia | 5 | | | |
| Monoethanolamine | 2 | | | |
| Propylene glycol | 8 | | | |
| Polyoxyethylene (20) isostearyl ether | 24 | | | |
| Polyoxyethylene (2) isostearyl ether | 20 | | | |
| "Merquat 280" (trade name; product of Calgon Corp., a 35 wt. % aqueous solution) | 8 | | | |
| "Polymer JR400" (trade name; product of Union Carbide) | | 0.5 | | 0.5 |
| "Amodimethicone SM8702C" (trade name; product of Dow Corning Toray Silicone) | | | 2 | |
| "Polyether modified silicone KF6005" (trade name; product of Shin-Etsu Chemical) | | | | 0.3 |
| Tetrasodium ethylenediaminetetraacetate | 0.1 | | | |
| Perfume | q.s. | | | |
| Ammonium chloride | Amount to adjust pH to 10 | | | |
| Water | Balance | | | |
| 2nd part | | | | |
| 35 wt. % aqueous hydrogen peroxide | 17.1 | | | |
| Methylparaben | 0.1 | | | |
| Phosphoric acid | Amount to adjust pH to 3.5 | | | |
| Water | Balance | | | |

Examples 10 to 12

In a manner known per se in the art, hair dyes as shown in Table 3 were prepared. The data appearing in Table 3 is represented by wt. %.

TABLE 3

|  | Examples | | |
|---|---|---|---|
|  | 10 | 11 | 12 |
| 1st part | | | |
| Toluene-2,5-diamine | 2 | 1 | |
| Para-aminophenol | | | 1 |
| Resorcin | 0.9 | 1.1 | |
| Para-amino-ortho-cresol | 0.5 | | 1.1 |
| 2,4-Diaminophenoxyethanol | 0.7 | | |
| Dye [Compound (a)] | 0.05 | | |
| Dye [Compound (b)] | | 0.15 | |
| Dye [Compound (c)] | | | 0.1 |
| 28 wt. % aqueous ammonia | 5 | | |
| Monoethanolamine | 2 | | |
| Propylene glycol | 8 | | |
| Polyoxyethylene (20) isostearyl ether | 24 | | |
| Polyoxyethylene (2) isostearyl ether | 20 | | |
| "Merquat 280" (trade name; product of Calgon Corp., a 35 wt. % aqueous solution) | 8 | | |
| "Polymer JR400" (product of Union Carbide) | | 0.5 | |
| "Amodimethicone SM8702C" (trade name; product of Dow Corning Toray Silicone) | | | 2 |
| Sodium sulfite | 0.05 | | |
| Ascorbic acid | 0.5 | | |
| Tetrasodium ethylenediaminetetraacetate | 0.1 | | |
| Perfume | q.s. | | |
| Ammonium chloride | Amount to adjust pH to 10 | | |
| Water | Balance | | |

TABLE 3-continued

|  | Examples | | |
|---|---|---|---|
|  | 10 | 11 | 12 |
| 2nd part | | | |
| 35 wt. % Aqueous hydrogen peroxide | 17.1 | | |
| Methylparaben | 0.1 | | |
| Phosphoric acid | Amount to adjust pH to 3.5 | | |
| Water | Balance | | |

Example 13

In a manner known per se in the art, the following hair dye was prepared.

|  | (wt. %) |
|---|---|
| (First part) | |
| Para-aminophenol | 1 |
| Para-amino-ortho-cresol | 1.1 |
| Compound (a) | 0.1 |
| 28 wt. % aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |
| (Second part) | |
| 35 wt. % Hydrogen peroxide | 17.1 |
| Methylparaben | 0.1 |
| Phosphoric acid | Amount to adjust pH to 3.5 |
| Water | Balance |

What is claimed is:

1. A method for dyeing hair comprising applying to the hair a dye composition an oxidzing agent and direct dye compound having the formula (I).

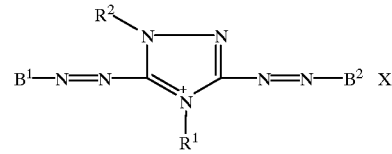

(1)

following formula (2), (3), (4) or (5):

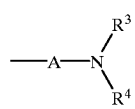

(2)

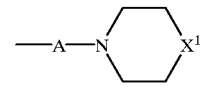

(3)

-continued (4)

(5)

wherein A represents a phenylene group which may have an unionizable substituent, or a naphthylene group; $R^3$ and $R^4$ are the same or different and each independently represents a hydrogen atomm, a $C_{1-4}$alkyl group which may have a substituent, an aralkyl group or a phenyl group, $X^1$ represents an oxygen atom, an imino group or a methylene group, $X^2$ represents an ethylene or trimethylene group which may have a substituent, Y represents a $C_{1-4}$alkyl or an arakyl group, $R^6$ represents a hydrogen atom or a $C_{1-4}$alkyl group and $R^7$ represents a hydrogen atom or an unionizable group;

$R^1$ and $R^2$ are the same or different and each independently represents a $C_{1-4}$alkyl group a carbamoylethyl group, a 2-carbamoylpropyl group, a benzyl group or a group of formula (6) or (7):

(6)

—CH$_2$CHCH$_2$R$^8$
       |
       X$^3$ (7)

—CH$_2$CHR$^9$
       |
       X$^3$ wherein, $X^3$ represents a hydroxyl group, an amino group or a thiol group, $R^8$ represents a hydrogen atom, a halogen atom, a $C_{1-4}$alkyl group which may have a substituent, a $C_{1-4}$alkoxy group or a phenoxy group, and $R^9$ represents a hydrogen atom or a phenyl group which may have a substituent; and $X^-$ represents an anion.

2. The method according to claim 1, wherein the hair dye composition further comprises an oxidation dye.

3. The method according to claim 1, wherein the anion X is chloride, bromide, iodide, trichlorozinic acid ions, tetrachlorozinic acid ions, sulfuric acid ions, hydrosulfuric acid ions, methyl sulfate ions, phosphoric acid ions, formic acid ions or acetic acid ions.

4. The method according to claim 1, wherein the pH of the hair dye composition is adjusted to a pH of 6 to 11 by addition of alkali in an amount of 0.01 to 20 wt %.

5. The method according to claim 5, wherein the amount of alkali added ranges from 0.1 to 10 wt %.

6. The method according to claim 1, wherein the hair dye composition contains an amount of 0.01 to 20 wt % of direct dye 1).

7. The method according to claim 1, wherein the direct dye (1) of the hair dye composition is a member selected fromt the group consisting of

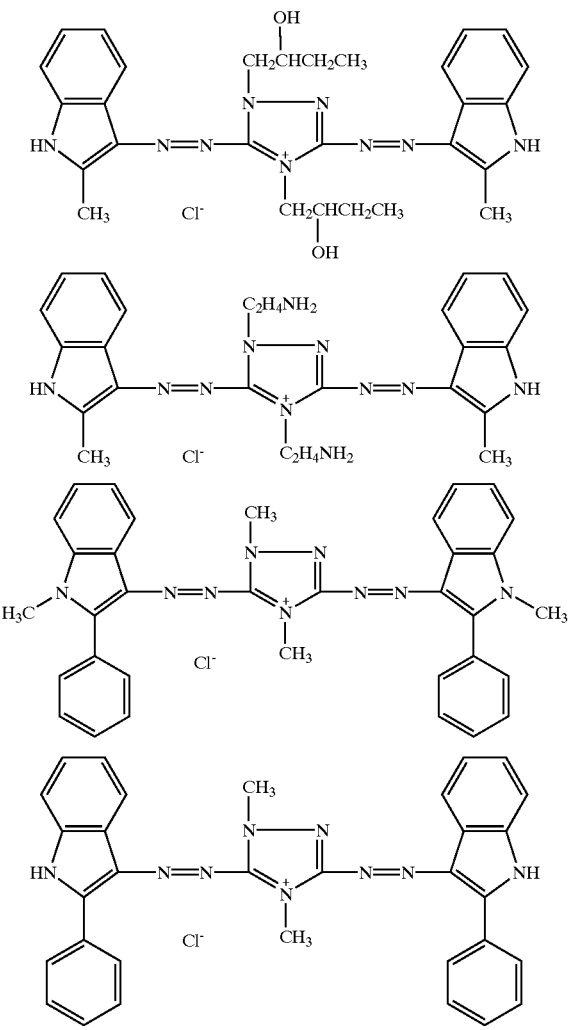

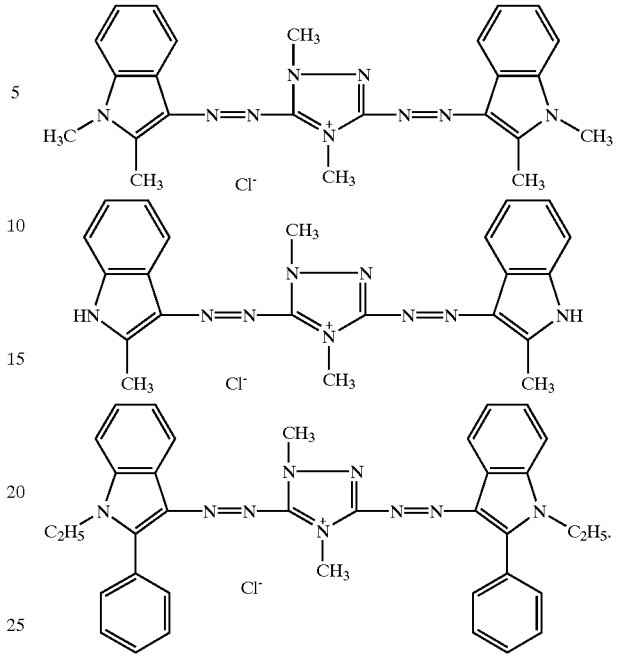

8. The method according to claim 5, wherein divalent radical A is phenylene, chlorophenylene, acetylaminophenylene, methlphenylene, methoxphenylene or napthylene; $R^3$ and $R^4$ hydrogen, methyl, ethyl, cyanoethyl, hydroxyethyl, benzyl, phenyl, methoxyethyl or chloroethyl; $X^2$ is trimethylene, 2-hydroxytrimethylene, 2-chlorotrimethylene 2-methoxy, propylene or 1,1,2-trimethylene; Y is methyl, butyl, bromoethyl or benxyl; $R^5$ is methyl, ethyl, pheyl or tolyl; $R^6$ hydrogen, methyl or ethyl and $R^7$ is methyl, chloro or methoxy.

9. The method according to claim 1, wherein $C_{1-4}$ alkyl of $R^1$ and $R^2$ is methyl or ethyl and $R^8$ is methyl, phenoxy, chloro, methacryloyloxy, butoxy, ethoxy or bromo.

\* \* \* \* \*

UNITED STATES PATENT AND TRADEMARK OFFICE
CERTIFICATE OF CORRECTION

PATENT NO. : 6,451,069 B2  
DATED : September 17, 2002  
INVENTOR(S) : Kenichi Matsunaga et al.

It is certified that error appears in the above-identified patent and that said Letters Patent is hereby corrected as shown below:

Column 12,  
Line 44, "composition an" should read -- composition comprising an --;  
Line 55, "following formula (2), (3), (4), or (5): should read -- wherein $B^1$ and $B^2$ are the same or different and each independently represents a group of the formula (2), (3), (4), or (5): --

Column 13,  
Line 19, "atomm" should read -- atom --;  
Line 51, "X" should read -- $X^-$ --;  
Line 60, "according to claim 5" should read -- according to claim 1 --;  
Line 63, "1)" should read -- (1) --;  
Line 67, "fromt" should read -- from --.

Column 16,  
Line 28, "according to claim 5" should read -- according to claim 1 --;  
Line 31, "and $R^4$" should read -- and $R^4$ are --  
Line 33, "2-methoxy" should read -- , 2-methoxytrimethylene --;  
Line 34, "trimethylene" should read -- trimethylethylene --  
Line 34, "benxyl" should read -- benzyl --  
Line 35, "pheyl" should read -- phenyl -- and  
Line 35, "$R^6$ hydrogen" should read -- $R^6$ is hydrogen --, Signed and Sealed this First Day of April, 2003

JAMES E. ROGAN  
*Director of the United States Patent and Trademark Office*